April 4, 1972 J. S. SWEET Plant Pat. 3,094
ROSE PLANT
Filed Feb. 9, 1970
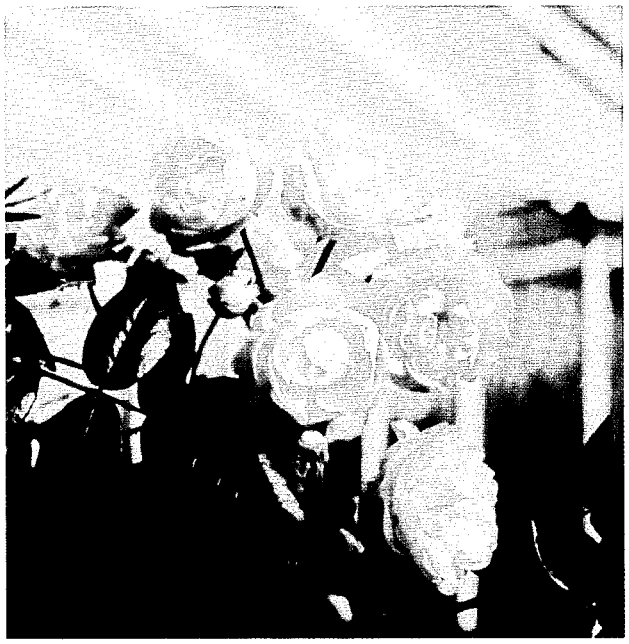
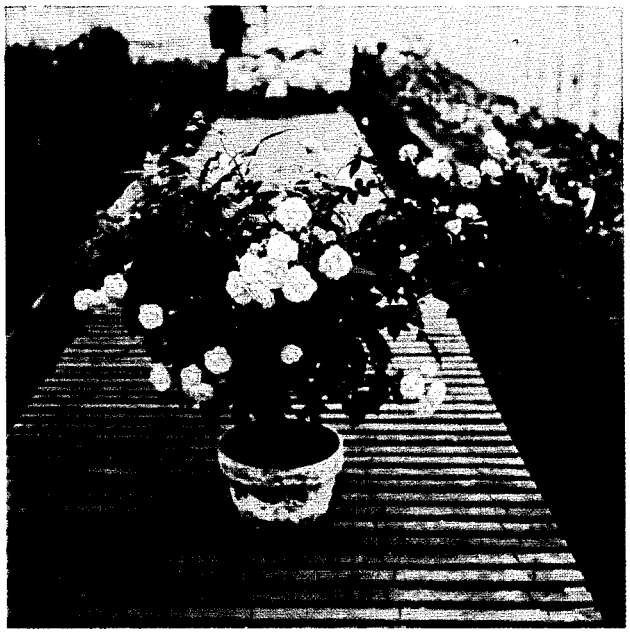
INVENTOR.
JACK S. SWEET
BY Rummler & Snow
Attys.

United States Patent Office

Plant Pat. 3,094
Patented Apr. 4, 1972

3,094
ROSE PLANT
Jack S. Sweet, St. Petersburg, Fla., assignor to
Geo. J. Ball, Inc., West Chicago, Ill.
Filed Feb. 9, 1970, Ser. No. 10,059
Int. Cl. A01h 5/00
U.S. Cl. Plt.—26 1 Claim

ABSTRACT OF THE DISCLOSURE

A new variety of rose plant originating as a sport of Mother's Day (unpatened) and characterized by its very delicate French Rose coloration and its adaptability to greenhouse pot-forcing culture.

BACKGROUND OF THE INVENTION

This new variety of rose plant was discovered by me at Pinellas Park, Fla., in March 1966, in the course of my work in connection with propagation and growth, for commercial purposes, of the parent variety "Mother's Day." The new variety originated as a sport of the parent variety grown on greenhouse bench and was noticed because of its very distinctive French Rose coloration, a feature which, coupled with the other characteristics of the parent, was believed to have strong commercial merit. Asexual propagation of this sport by budding, through successive generations, at Hamilton City, Calif., has demonstrated that the distinctive characteristics of this new variety of rose plant are fixed and hold true. At present, propagation for commercial purposes is carried on, by budding, at Hamilton City, Calif.

DESCRIPTION OF THE DRAWING

My new variety of rose plant is shown in the accompanying full color photographic drawing in which the upper view is a close-up of the blooms and foliage showing the form of fully opened flowers and buds, and the lower view shows an entire plant illustrating its growth habit and form.

DESCRIPTION OF THE NEW PLANT

The following is a detailed description of the new variety of rose plant with color specification according to the Horticultural Colour Chart of the British Colour Council.

The plant

Origin: Sport.
Parentage: "Mother's Day" (unpatented).
Classification: Botanic—Polyantha. Commercial—Greenhouse pot forcing.
Form: Bush.
Height: To 2½ feet.
Growth: Vigorous and upright.
Branching: Much branched with good strength.
Foliage: Quantity—abundant.
*Leaf size.*—3 inches wide. Shape: Odd pinnate.
*Leaflets.*—5 to 7 in number. Shape: Ovate with serrated margins. Texture: Smooth. Color: Upper side, Spinach Green 0960. Under side, Spinach Green 0960/3.
*Petiols.*—½ to ¾ inch long.
*Rachis.*—Hairy, grooved.
*Prickles.*—Reddish Brown in color (general color meaning) and of moderate size.

The bud

Form: Ovoid.
Size: Small.
*Diameter.*—7/16 to ½ inch.
*Depth.*—⅜ to ½ inch.
Bud opens slowly.
Color: When sepals first divide—Geranium Lake 20/2. When sepals begin to unfurl—Slightly lighter than Geranium Lake 20/2.
Sepals: Spear shaped and curl back.
Peduncle: Erect, smooth, and 1½ to 1¾ inches long.

The flower

Blooming habit: Continuous and profusely through all seasons.
Size: Small. Diameter—1½ inches.
Borne: In clusters—same as parent.
Shape: High center. Form changes to shallow cupped as bloom matures.
Petalage: Number of petals—20 to 25.
*Arrangement.*—Regular imbricated.
*Form.*—Obovate, usually with a shallow notch.
*Color.*—Outer petal, French Rose 520/1 edged with Geranium Lake 20/2. Base—Near White. Inside petal, French Rose 520/1, Reverse side, French Rose 520/1.
*Texture.*—Soft.
Petaloids: Number—Variable, 2 to 6.
*Size.*—Small.
*Color.*—White at base leading into French Rose 520/1.
Peduncle: Upright. 1½ to 1¾ inches long.
*Color.*—Lettuce Green 861.
Effect of weather: Bloom is slightly lighter in color in hot weather.
Persistence: Cleans slowly. Petals stay on stem 7 to 10 days.
Fragrance: Very slight
Lasting quality: On plant—7 to 10 days. As cut flowers—4 to 5 days; sometimes longer.

Reproductive organs

Stamens: Anthers—Many in number, of irregular length, and regular arrangement. Filaments—3/16 to 5/16 inch long, Greenish Yellow in color (general color term).
Pollen: Color—Yellow (general color description).
Pistils: Several in number, variable in length.
Stigmas: Color—Greenish Yellow (general description).

My new variety of rose plant resembles "Mother's Day" (unpatented) in all respects except color and in that regard, the French Rose coloration of the blooms of the new variety is unique and highly desirable for greenhouse and pot-forcing purposes.

I claim:

1. A new and distinct variety of rose plant substantially as herein shown and described, characterized by the unique French Rose coloration of its blooms.

No references cited.

ROBERT E. BAGWILL, Primary Examiner